United States Patent [19]

Mitchell

[11] Patent Number: 4,623,264

[45] Date of Patent: Nov. 18, 1986

[54] TEMPERATURE SENSING USING ULTRASONIC SYSTEM AND MOVABLE TARGET

[75] Inventor: Thomas Mitchell, Richardson, Tex.

[73] Assignee: Southland Corporation, Dallas, Tex.

[21] Appl. No.: 727,911

[22] Filed: Apr. 26, 1985

[51] Int. Cl.[4] .................. G01N 29/02; G01K 11/22; G01F 23/28

[52] U.S. Cl. .................. 374/117; 73/1 DV; 73/1 H; 73/292; 374/142

[58] Field of Search ................ 374/117, 142, 1; 73/1 DV, 1 H, 292

[56] References Cited

U.S. PATENT DOCUMENTS

| | | | |
|---|---|---|---|
| 3,015,955 | 1/1962 | Argabrite | 374/205 |
| 3,290,944 | 12/1966 | Altman et al. | 73/290 V |
| 3,403,509 | 10/1968 | Eastman et al. | 73/290 V |
| 3,501,956 | 3/1970 | Yamaga et al. | 73/290 V |
| 3,593,818 | 7/1971 | Pohlmann et al. | 73/290 V |
| 3,633,423 | 1/1972 | Bell | 73/290 V |
| 3,878,502 | 4/1975 | Rochelle | 73/290 V |
| 4,141,247 | 2/1979 | Schlick | 374/205 X |
| 4,197,741 | 4/1980 | Morrow, Jr. | 73/290 V X |
| 4,235,099 | 11/1980 | Ishizaka | 73/290 V |
| 4,320,659 | 3/1982 | Lynnworth et al. | 73/290 V |
| 4,337,656 | 7/1982 | Rapp | 73/290 V |
| 4,430,883 | 2/1984 | Auphan | 73/1 DV |
| 4,442,700 | 4/1984 | Swoboda | 73/290 V |
| 4,470,307 | 9/1984 | Genter | 73/1 DV |
| 4,483,630 | 11/1984 | Varela | 73/290 V |
| 4,535,628 | 8/1985 | Hope | 73/290 V |

FOREIGN PATENT DOCUMENTS 0053428 5/1981 Japan .................. 374/142

OTHER PUBLICATIONS

"Cryogenic Level-Measuring Calibration System with Thermal Stabilization of the Transducer Mounting", A. L. Seifer et al, Measurement Techniques-vol. 25, No. 1, Jan. 1982, pp. 59-61.

*Primary Examiner*—Daniel M. Yasich
*Attorney, Agent, or Firm*—Cushman, Darby & Cushman

[57] ABSTRACT

An ultrasonic transducer for emitting and receiving sound pulses is mounted within a fluid whose temperature is to be determined. The transducer is disposed in operative association with a first target which is mounted by a bimetallic coil so that it moves in a known manner with respect to the transducer in response to changes in temperature in the fluid. A stationary target is also provided disposed a fixed, known distance from the transducer, for calibration purposes. The transducer is mounted within a fiberglass tube, as are the movable and stationary targets. The tube may be mounted at the bottom of a liquid (e.g. gasoline) storage tank with the transducer facing upwardly so that both the level of liquid within the tank, and the density of the liquid as related to temperature, can be determined utilizing the transducer and a computer for acting upon the transducer output.

21 Claims, 3 Drawing Figures

U.S. Patent   Nov. 18, 1986   4,623,264
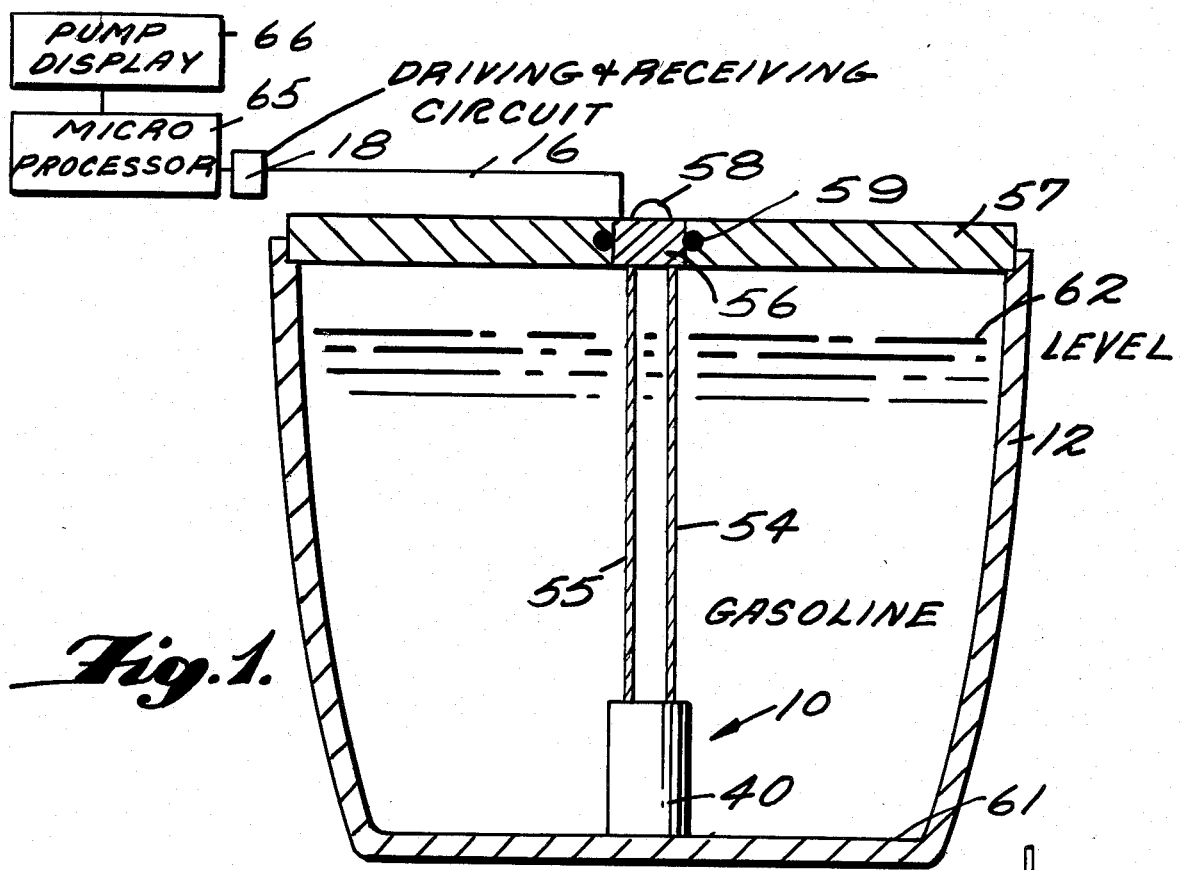
Fig. 1.
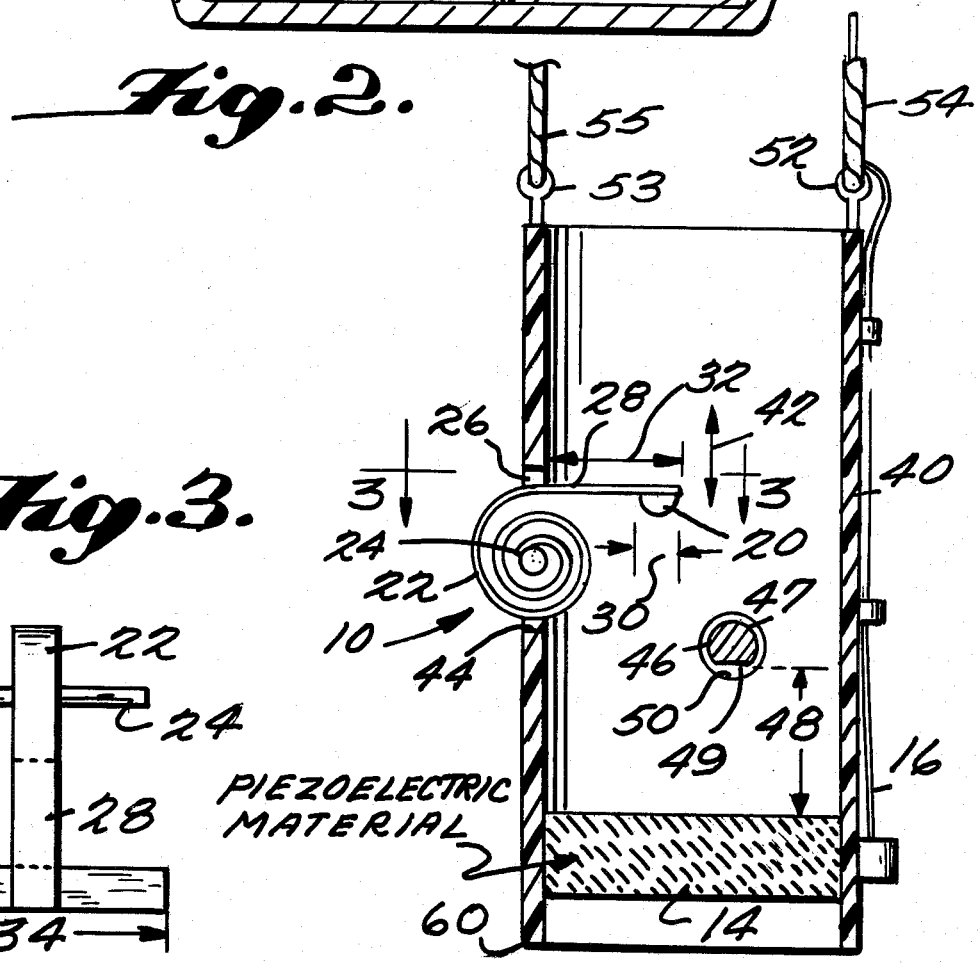
Fig. 2.
Fig. 3.

4,623,264

TEMPERATURE SENSING USING ULTRASONIC SYSTEM AND MOVABLE TARGET

BACKGROUND AND SUMMARY OF THE INVENTION

The invention relates to a method and apparatus for sensing the temperature of a fluid utilizing a transmitting and receiving transducer (such as piezoelectric material which converts electrical pulses to pulses of ultrasonic energy and vice-versa) for emitting and receiving sound pulses. While the invention has applicability for the sensing of the temperature of the surrounding fluid in a wide variety of environments, the invention is particularly useful in association with a system for monitoring the level of liquid within a liquid holding tank, such as the amount of gasoline in a gasoline tank at a service station or the like. It has been found that an ultrasonic transducer is eminently suited for liquid level monitoring, and according to the invention the same transducer utilized to monitor the liquid level can be utilized to determine the temperature of the liquid.

For the particular application where the invention is utilized with a liquid level monitoring system, a number of functional advantages result. Gasoline, and other liquids, of course, expand and contract with temperature, and for large storage tanks such an expansion and contraction can result in a considerable change in the volume of gasoline within the tank. The gasoline tank monitoring systems commonly used desirably are useful in detecting leaks of gasoline from the tank. So that such systems do not falsely indicate leakage of gasoline due to contraction as a result of temperature changes, it is necessary to determine the temperature of the gasoline and to compensate for the temperature in determining the amount of gasoline within the tank. Then a true value of the amount of gasoline within the tank can be determined. The invention can also be used to verify that the amount of gasoline to be delivered to the tank has been delivered.

According to a specific aspect of the present invention, a method of determining the volume of gasoline (or other liquid) in a tank is provided. The method is practiced utilizing a transmitting and receiving transducer for emitting and receiving sound pulses, and a movable target. The method comprises the steps of: Disposing the transducer and movable target in the liquid within the tank so that sonic pulses emitted by the transducer impact upon, and are reflected by, the movable target and pass through the air-liquid interface. Mounting the movable target so that it moves in response to temperature of the liquid in a known manner with respect to the transducer. Emitting sound pulses from the transducer so that they reflect off the movable target and reflect back from the air-liquid interface; and, using the reflected sound pulses received by the transducer to determine the level of liquid within the tank, and the density of the liquid as related to the temperature of the liquid, to thereby calculate the amount of liquid within the tank.

According to a more general method within the scope of the present invention, a method of sensing temperature of a fluid is provided. The method utilizes a transducer and a movable target. The method comprises the steps of: Disposing the transducer and movable target within the fluid or liquid whose temperature is to be sensed. Mounting the movable target with respect to the transducer so that the target moves in response to temperature changes in the fluid in a known manner with respect to the transducer; and, emitting and receiving sound pulses with the transducer so that the sound pulses reflect off of the target and back to the transducer to thereby allow calculation of the distance of the moveable target from the transducer, and thus the temperature of the fluid. The method also preferably comprises the step of calibrating the transducer (for instance so that it is not affected by differences in the particular properties of the fluid) by providing a second stationary target for the transducer, mounted a fixed known distance from the transducer.

The fluid temperature sensing apparatus according to the present invention comprises the following elements: (a) Transmitting and receiving transducer means for emitting and receiving sound pulses. (b) A first target for reflecting sound pulses emitted by the transducer means. (c) Temperature responsive means affixed to the first target for moving the target in a known manner in response to temperature changes in the fluid. The temperature responsive means preferably comprises a coil of bimetallic material stationarily mounted on one end thereof with respect to the transducer, and having a lever at the other end thereof, the lever affixed to the target, which may comprise a stainless steel generally cylindrical member. And, (d) means for mounting the temperature responsive means in operative association with the transducer means so that the target moves toward and away from the transducer means in a known manner in response to changes in temperature in the fluid. The mounting means preferably comprises a tube of rigid material (such as fiberglass), with the transducer mounted within the tube, and with the coil mounted to the tube so that the first target is within the tube. Also, to effect calibration of the system, a second, stationary target preferably is provided. The second target is mounted to the tube so that it is within the tube and is spaced a fixed, known distance from the transducer.

The invention also comprises the abovementioned components mounted so that the tube is at the bottom of a liquid (e.g. gasoline) holding tank so that sound pulses emitted from and received by the transducer pass to and from the air-liquid interface within the tank. The information received by the transducer from the movable and stationary targets, and from the air-liquid interface, is utilized by a microcomputer to determine the amount of liquid within the tank.

It is the primary object of the present invention to provide a simple and effective mechanism and procedure for determining the temperature of a fluid, which is particularly useful in determining the amount of liquid in a liquid holding tank. This and other objects of the invention will become clear from an inspection of the detailed description of the invention, and from the appended claims.

BRIEF DESCRIPTION OF THE DRAWINGS

FIG. 1 is a side schematic of exemplary apparatus according to the present invention in association with a gasoline storage tank (shown in cross-section);

FIG. 2 is a detail side cross-sectional view of exemplary fluid temperature sensing apparatus according to the present invention; and FIG. 3 is a front detail view of the movable target apparatus of FIG. 2 taken along line 3—3 of FIG. 2.

DETAILED DESCRIPTION OF THE DRAWINGS

Exemplary fluid temperature sensing apparatus according to the present invention is shown generally by reference numeral 10 in FIGS. 1 and 2. In FIG. 1 the apparatus 10 is shown in operative association with a gasoline storage tank 12 for determining the amount of gasoline within the tank 12.

FIGS. 2 and 3 illustrate the details of the apparatus 10. A first main component of the apparatus 10 comprises a transmitting and receiving transducer means 14 for emitting and receiving sound pulses. The transducer 14 may be selected from a wide variety of conventional structures. For instance it may comprise a piezolectric material that is capable of converting an electrical pulse to a pulse of ultrasonic energy, and vice-versa. The actual transducer 14 itself is connected by electrical wires 16 or the like to conventional driving and receiving circuitry 18 (see FIG. 1). Conventional piezolectrics and circuitry are disclosed in U.S. Pat. No. 3,290,944, the disclosure of which is hereby incorporated by reference herein. While the transducer means is shown in the drawings as a single unit 14, it may be constructed as separate emitter and receiver units.

Another primary component of the apparatus 10 comprises a first target 20 (see FIGS. 2 and 3) for reflecting sound pulses from the transducer 14 back to it. The first target 20 is a movable target. It is made movable by a third primary component of the apparatus 10, namely a temperature responsive means which is affixed to the target 20 for moving it in a known manner in response to temperature changes in the fluid (e.g. liquid gasoline in tank 12).

The temperature responsive means preferably takes the form of a bimetallic material, such as the spiral bimetallic coil 22. Any suitable conventional bimetallic coil 22 can be utilized, such as one produced by GTE Technical Products and sold under the name "Chance 2400". In use, the coil 22 is affixed at one end thereof to a stationary pin 24, and at the other end thereof is affixed, at point 26 (see FIG. 2), to a lever 28. The lever 28 is affixed at the free end thereof to the target 20. In the preferred embodiment illustrated in the drawings the target 20 comprises a generally cylindrically shaped member of stainless steel.

The specific dimensions, etc., of the target, and related components, are not particularly critical, and may be varied widely so long as they perform their intended function. In one particular exemplary embodiment, the effective width 30 of the target 20 would be 0.4 inches, the length 32 of the lever 28 would be 1 inch±0.25 inches, the diameter of the pin 24 would be 0.156 inches, the length of the pin 24 would be 0.5 inches, and the length 34 of the target 20 would be 1.2 inches.

The apparatus 10 also comprises a tube as for example a portable container-like device 40. or equivalent structure, for mounting the temperature responsive means 22. That is the tube 40, which is of a rigid material that will not significantly corrode in the fluid with which it is utilized (e.g. fiberglass), mounts the pin 24 connected to the bimetallic coil 22 in operative association with the transducer 14 so that the target 20 moves toward and away from the transducer (see arrow 42 in FIG. 2) in a known manner in response to temperature. An increase or decrease in the temperature of the fluid causes the bimetallic coil 22 to move the lever 28 in such a way that it moves generally linearly in the dimension of arrows 42, toward and away from the transducer. In a preferred embodiment, the transducer 14 has basically the same external configuration and dimensions as the internal configuration and dimensions of the tube 40, and the pin 24 is glued or otherwise affixed at the opposite ends thereof to a cut-out 44 within the wall of the tube 40 so that the lever 28 extends generally radially into the interior of the tube 40.

In order to provide effective calibration of the apparatus 10 so that the proper sensing will be determined irrespective of the particular properties of the fluid whose temperature is being sensed, a calibration means is provided. The calibration means preferably takes the form of a second, stationary target 46 mounted within the tube 40, and spaced a fixed known distance 48 from the transducer 14. The target 46 preferably comprises a brass screw which has threads 47 and a flattened face 49. Threads 47 are threaded into openings (e.g. opening 50) on opposite sides of tube 40, so that the face 49 extends completely through the diameter of the tube. A wide variety of other configurations are possible, but a flattened face (like 49) in operative association with transducer 14 is desirable. Because the second target 46 is a known distance 48 from the transducer 14, the speed of sound within the fluid (e.g. the gasoline in tank 12) may be easily determined, and that information utilized in subsequent determinations of temperature (proportional to the amount of movement of the movable target 20 in dimension 42), and ultimately, for example, the volume of gasoline within the tank 12.

According to the present invention, the apparatus 10 may be utilized in association with apparatus for determining the amount of liquid within the holding tank 12. With reference to FIGS. 1 and 2, this is accomplished by attaching the tube 40 through suitable structures, such as metal eyelets 52, 53, to suitable thin tubes, or cables, 54, 55. The tubes or cables 54, 55 are connected to a lid 56 which is adapted to fit within the cover 57 for the tank 12. A handle 58 or the like may be provided on the lid 56 to facilitate movement thereof, and an O-ring, or other suitable sealing means 59, may be provided to seal the lid 56 to the cover 57 so that there is no emission of vapors, or the like, from the tank 12. The electrical wire 16 extending from the transducer 14 to the circuitry 18 passes within the tube or cable 54, through the lid 56.

Alternatively, fiberglass tube 40 could extend the entire height of the tank 12, from lid 56 to the bottom 61. It would have a plurality of holes along its length to allow free flow of liquid therein. In this case the tube provides a "stilling well", which facilitates the level sensing function.

In the use of the apparatus 10, it is disposed within the tank 12 so that the end 60 (see FIG. 2) of the tube 40 abuts the bottom 61 of the tank 12, and rests thereon. In this orientation, the tube 40 is of course substantially vertical, and sound pulses emitted and received thereby pass upwardly through the volume of gasoline within the tank 12 to and through the gas-liquid interface 62 at the top surface of the gasoline within the tank 12. Thus sound pulses emitted by transducer 14 are reflected off of, and returned to the transducer, from all of movable target 20, stationary target 46, and the air-liquid interface 62.

The information received from the transducer 14, transmitted to the receiving circuitry 18, is operated upon to determine the amount of liquid within the tank 12, and to make various adjustments to other equipment dependent upon such a determination, if desired. This is preferably accomplished by operatively connecting a conventional microprocessor 65, or other computing means, to the receiving circuitry 18 output (see FIG. 1). The microprocessor performs the necessary calculations which transform the sound pulses received by the transducer 14 into determinations of the temperature (which is related to density) of the liquid, and the level of the liquid within the tank 12, to determine the amount of liquid within the tank. This provides effective monitoring of the liquid within the tank, so that it can be known if any leakage occurs. It also allows control of a pump for dispensing the liquid, and/or a display, 66, the exact calibration of which is dependent upon the temperature (density) of the gasoline.

Operation

Utilizing the apparatus 10, it will be readily seen that the method of sensing the temperature of a fluid, and for determining the amount of liquid within a tank, may be provided.

For sensing the temperature of a fluid utilizing the apparatus 10, one merely disposes the tube 40 within the fluid whose temperature is to be determined. The bimetallic coil 22 is mounted by pin 24 to the tube 40 so that the movable target 20 moves toward and away from (see arrows 42) the transducer 14. Sound pulses emitted by the transducer reflect off of the movable target 20 and back to the transducer 14. The distance the sound pulses travel before being reflected is dependent upon the temperature since the coil 22 will move the target 20 toward and away from the transducer 14 in response to temperature. Of course the distance of travel of the sound pulses is proportional to the time it takes for them to travel to the target 20 and back, and utilizing this information and the speed of sound within the fluid, one can readily calculate temperature changes. Calibration of the transducer 14 by determining the particular speed of sound within the fluid is preferably accomplished by utilizing the stationary target 46 which is a known distance 48 from the transducer 14.

The sensing that is provided according to the present invention can be continuous or intermittent. In a preferred embodiment, however, every 20 milliseconds or so, pulses are sent out by the transducer 14. Every 16 pulses received by the transducer 14 are then averaged, utilizing the microprocessor 65, to get an accurate determination, and this average is then displayed, used to control a pump, and/or used in further calculations by the microprocessor 65, as desired.

The temperature sensing set forth above is also utilized as part of the method for determining the volume of liquid (e.g. gasoline) within the tank 12. The apparatus 10 is lowered so that the end 60 of the tube 40 abuts the bottom 61 of the tank 12, and the lid 56 is sealed in place. The driving and receiving circuitry 18 controls transducer 14 and receives information therefrom, which includes the information from the stationary and movable targets 46, 20, and also reflections from the air-liquid interface 62. The reflections from the interface 62 are used in calculating the level of gasoline within the tank since the distance of the transducer 14 from the interface 62 is proportional to the time between emission and receipt of a pulse, and since the speed of sound within the liquid is known, and since the configuration (and thus volume) of the tank up to the interface 62 are known. The microprocessor 65 utilizes the information from the transducer 14 regarding reflections from each of the elements 20 and 46, and the interface 62, to thereby compute the amount of liquid within the tank 12.

It will thus be seen that according to the present invention a simple and effective method and apparatus are provided for sensing the temperature of a fluid, and determining the amount of liquid within a tank. While the invention has been herein shown and described in what is presently conceived to be the most practical and preferred embodiment thereof, it will be apparent to those of ordinary skill in the art that many modifications may be made thereof within the scope of the invention, which scope is to be accorded the broadest interpretation of the appended claims so as to encompass all equivalent structures and procedures.

What is claimed is:

1. A fluid temperature sensing apparatus comprising:
   (a) transmitting and receiving transducer means for emitting and receiving sound pulses;
   (b) a first target for reflecting sound pulses emitted by the transducer means;
   (c) temperature responsive means affixed to said first target for moving the target in response to temperature changes in the fluid; and
   (d) means for mounting said temperature responsive means at a predetermined distance from said transducer means so that said target moves toward and away from said transducer means in response to changes in temperature in the fluid.

2. Apparatus as recited in claim 1 wherein said temperature responsive means includes bimetallic material.

3. Apparatus as recited in claim 2 further comprising a second target, said second target stationarily mounted to said mounting means a known, fixed, distance from said transducer means.

4. Apparatus as recited in claim 2 wherein said bimetallic material comprises a coil of bimetallic material having a first end fixed to said mounting means, and a second end connected to a lever, and wherein said lever is affixed to said first target.

5. Apparatus as receited in claim 4 wherein said target comprises a stainless steel, cylindrically-shaped member.

6. Apparatus as recited in claim 4 wherein said means for mounting includes a tube of relatively rigid material, and wherein said transducer means are mounted within said tube, and wherein said temperature responsive means are mounted to said tube so that said first target is within said tube.

7. Apparatus as recited in claim 6 further comprising a second target, said second target stationarily mounted to said tube, within said tube, a known, substantially fixed, distance from said transducer means.

8. Apparatus as recited in claim 6 further comprising means for calibrating said transducer means, so that the temperature sensed by said apparatus is accurate irrespective of the fluid properties.

9. Apparatus as recited in claim 8 wherein said calibrating means comprises a second target stationarily mounted to said tube so that it is within said tube, and is positioned a substantially fixed, known distance from said transducer means; and computer means for acting upon the pulses received by said transducer means.

10. Apparatus as recited in claim 1 further comprising means for calibrating said transducer means, so that the temperature sensed by said apparatus is accurate irrespective of the fluid properties.

11. Apparatus as recited in claim 10 wherein said calibrating means comprises a second target stationarily mounted to said mounting means so that it is a substantially fixed, known distance from said transducer means; and computer means for acting upon information received by said transducer means.

12. Apparatus as recited in claim 1 wherein said means for mounting inclues a tube of relatively rigid material, and wherein said transducer means are mounted within said tube, and wherein said temperature responsive means are mounted to said tube so that said first target is within said tube.

13. Apparatus as recited in claim 12 further comprising a second target, said second target stationarily mounted, to said tube, within said tube, a known, substantially fixed, distance from said transducer means.

14. Apparatus for determining the amount of liquid within a liquid holding tank comprising:
  (a) transmitting and receiving transducer means for emitting and receiving sound pulses;
  (b) a first target for reflecting sound pulses emitted by the transducer means;
  (c) temperature responsive means affixed to said first target for moving the target in response to temperature changes in the fluid;
  (d) mounting means for mounting said transducer means within a liquid holding tank having a liquid therein and an air-liquid interface so that the transducer means is positioned with respect to the air-liquid interface to emit and receive sound pulses to and from said air-liquid interface; and for mounting said temperature responsive means at a predetermined distance from said transducer means so that said first target is positioned to reflect sound pulses from said transducer means;
  (e) computing means for receiving information from said transducer means, and for (1) calculating a level of liquid in the tank by the sound pulses received from said air-liquid interface, (2) calculating a density of liquid in the tank by the sound pulses reflected from said first target, and (3) calculated liquid level and liquid density.

15. Apparatus as recited in claim 14 further comprising means for calibrating said transducer means, so that the temperature sensed by said apparatus is accurate irrespective of the fluid properties.

16. Apparatus as recited in claim 15 wherein said mounting means includes a tube of relatively rigid material which will not easily corrode in the liquid within the tank; and wherein said transducer means are mounted within said tube, and said temperature responsive means mount said first target within said tube; and wherein said calibrating means comprises a second target affixed to said tube so that it is disposed within said tube a substantially fixed, known distance from said transducer means; and wherein said first and second target are mounted on said tube so that they are in-line with a line between said transducer means and the air-liquid interface.

17. Apparatus as recited in claim 16 wherein said temperature responsive means comprises a coil of bimetallic material affixed at a first end thereof to said tube, and having a lever affixed to a second end thereof, sad lever extending generally radially inwardly into said tube, said first target being affixed to said lever, and said lever comprising a material which does not easily corrode within the liquid in the tank.

18. A method of sensing the temperature of a fluid utilizing a transmitting and receiving transducer system for emitting and receiving sound pulses, and a movable target, comprising the steps of:
  (a) placing the transducer system and movable target within the fluid whose temperature is to be sensed;
  (b) mounting the movable target a predetermined distance from the transducer system so that the target moves relative to the transducer system in response to temperature changes in the fluid; and
  (c) emitting and receiving sound pulses with the transducer system so that the sound pulses emitted reflected off of the target and are received by the transducer system; and
  (d) calculating the distance of the movable target from the transducer, and calculating the temperature of the fluid from said distance.

19. A method as recited in claim 18 further comprising the step of (c) calibrating the transducer system for the particular properties of the fluid whose temperature is being sensed by providing a stationary target disposed a known distance from the transducer system, so that sound pulses emitted by the transducer system will also reflect off the stationary target and be received by the transducer system.

20. A method as recited in claim 18 wherein the fluid is liquid gasoline.

21. A method of determining the amount of liquid within a liquid holding tank utilizing a transmitting and receiving transducer system for emitting and receiving sound pulses, and a movable target, the liquid having a level within the tank and an air-liquid interface at the level; said method comprising the steps of:
  (a) positioning the transducer system and movable target in the liquid within the tank so that sonic pulses emitted by the transducer system impact upon, and are reflected by, the movable target and pass through the air-liquid interface;
  (b) mounting the movable target at a predetermined distance from said transducer system so that said target moves with respect to the transducer system in response to temperature of the liquid;
  (c) emitting sound pulses from the transducer system so that they reflect off the movable target and reflect from the air-liquid interface; and
  (d) using the reflected sound pulses received by the transducer system to calculate the level of liquid within the tank, and the density of the liquid as related to the temperature of the liquid, and to thereby calculate the amount of liquid within the tank from said level and said density.

* * * * *